(12) United States Patent
Saitou et al.

(10) Patent No.: US 8,278,471 B2
(45) Date of Patent: Oct. 2, 2012

(54) METHOD FOR PRODUCING RUTHENIUM COMPOUND

(75) Inventors: Ryuuichi Saitou, Tokyo (JP); Kang-go Chung, Tokyo (JP); Hideki Nishimura, Tokyo (JP); Tatsuya Sakai, Tokyo (JP); Sanshiro Komiya, Tokyo (JP); Naoto Noda, Tokyo (JP); Maki Nishiguchi, Tokyo (JP)

(73) Assignees: JSR Corporation, Tokyo (JP); Tri Chemical Laboratories Inc., Uenohara-shi (JP)

( * ) Notice: Subject to any disclaimer, the term of this patent is extended or adjusted under 35 U.S.C. 154(b) by 0 days.

(21) Appl. No.: 13/279,957

(22) Filed: Oct. 24, 2011

(65) Prior Publication Data

US 2012/0101290 A1   Apr. 26, 2012

(30) Foreign Application Priority Data

Oct. 25, 2010 (JP) ................. 2010-238625

(51) Int. Cl.
*C07F 15/00* (2006.01)

(52) U.S. Cl. ......................................... 556/13; 423/301
(58) Field of Classification Search ............... 556/13; 423/301
See application file for complete search history.

(56) References Cited

FOREIGN PATENT DOCUMENTS

WO   WO 2011/099467   *   8/2011

OTHER PUBLICATIONS

Von Th. Kruck, "Trifluorphosphin-Komplexe von Übergangsmetallen", Angew. Chem. 79, No. 1, 1967, pp. 27-43.

\* cited by examiner

*Primary Examiner* — Porfirio Nazario Gonzalez
(74) *Attorney, Agent, or Firm* — Oblon, Spivak, McClelland, Maier & Neustadt, L.L.P.

(57) ABSTRACT

A method for producing ruthenium compound including the step of reacting a compound represented by General Formula (1): $RuL^0_2$ (wherein $L^0$ represents an unsaturated hydrocarbon compound having 4 to 10 carbon atoms and at least two double bonds) with trifluorophosphine or reacting the compound represented by General Formula (1) with trifluorophosphine, and hydrogen or a halogen to obtain a compound represented by General Formula (2): $Ru(PF_3)_l(L^1)_m(L^2)_n$ (wherein $L^1$ represents a hydrogen atom or halogen atom, $L^2$ represents an unsaturated hydrocarbon compound having 4 to 10 carbon atoms and at least two double bonds, l is an integer from 1 to 5, m is an integer from 0 to 4, and n is an integer from 0 to 2, provided that l+m+2n=5 or 6). With this method, a trifluorophosphine-ruthenium compound can be synthesized under low-temperature and low-pressure conditions.

2 Claims, No Drawings

METHOD FOR PRODUCING RUTHENIUM COMPOUND

BACKGROUND OF THE INVENTION

1. Field of the Invention

The present invention relates to a method for producing ruthenium compound.

2. Description of the Related Art

Hexa(trifluorophosphine) ruthenium, tetrakis(trifluorophosphine) ruthenium dihydride and other trifluorophosphine-ruthenium compounds have been reported as ruthenium compounds (see Angew. Chem., 1967, 79, 27).

SUMMARY OF THE INVENTION

Trifluorophosphine-ruthenium compounds such as those described above are obtained by reacting ruthenium trichloride with trifluorophosphine. However, there was a problem that conditions of high temperature (120 to 300° C.) and high pressure (100 to 600 atm) are required.

In light of this problem, it is an object of the present invention to provide a method for synthesizing trifluorophosphine ruthenium compounds under low-temperature and low-pressure conditions.

As a result of research aimed at achieving this object, the inventors perfected the present invention after discovering that the object could be achieved by means of a trifluorophosphine-ruthenium compound manufacturing method which includes a step of reacting trifluorophosphine with the compound represented by General Formula (1) described below.

The method for producing ruthenium compound of the present invention includes the step of reacting a compound represented by General Formula (1) described below with trifluorophosphine, or reacting the compound represented by General Formula (1) described below with trifluorophosphine and at least one selected from hydrogen and halogen to obtain a compound represented by General Formula (2) described below:

$$RuL^0_2 \quad (1)$$

(in General Formula (1), $L^0$ represents an unsaturated hydrocarbon compound having 4 to 10 carbon atoms and at least two double bonds, and the two $L^0$ (i.e. $L^0$ and $L^0$) may be the same or different);

$$Ru(PF_3)_l(L^1)_m(L^2)_n \quad (2)$$

(in General Formula (2), $L^1$ represents a hydrogen atom or a halogen atom, and when there are more than one $L^1$, these $L^1$ may be the same or different, $L^2$ represents an unsaturated hydrocarbon compound having 4 to 10 carbon atoms and at least two double bonds, and when there are more than one $L^2$, these $L^2$ may be the same or different, l is an integer from 1 to 5, m is an integer from 0 to 4, and n is an integer from 0 to 2, provided that l+m+2n=5 or 6).

A trifluorophosphine-ruthenium compound can be synthesized under low-temperature and low-pressure conditions by the method for producing ruthenium compound of the present invention.

DESCRIPTION OF THE PREFERRED EMBODIMENTS

The present invention is explained in detail below.

The method for producing ruthenium compound of the present invention includes the step of reacting a compound represented by General Formula (1) described below with trifluorophosphine, together with hydrogen or halogen as necessary to obtain a compound represented by General Formula (2) described below:

$$RuL^0_2 \quad (1)$$

(in General Formula (1), $L^0$ represents an unsaturated hydrocarbon compound having 4 to 10 crbon atoms and at least two double bonds, and the two $L^0$ may be the same or different);

$$Ru(PF_3)_l(L^1)_m(L^2)_n \quad (2)$$

(in General Formula (2), $L^1$ represents a hydrogen atom or a halogen atom, and when there are more than one $L^1$, these $L^1$ may be the same or different, $L^2$ represents an unsaturated hydrocarbon compound having 4 to 10 carbon atoms and at least two double bonds, and when there are more than one $L^2$, these $L^2$ may be the same or different, l is an integer from 1 to 5, m is an integer from 0 to 4, and n is an integer from 0 to 2, provided that l+m+2n=5 or 6).

In General Formula (1), $L^0$ represents an unsaturated hydrocarbon compound having 4 to 10 carbon atoms and at least two double bonds.

Specific examples of $L^0$ include 1,3-pentadiene, 1,5-hexadiene, 1,4-hexadiene, 1,3-hexadiene, 2,4-hexadiene, 3-methyl-1,3-pentadiene, 2-methyl-1,4-pentadiene, 1,6-heptadiene, 1,5-heptadiene, 1,4-heptadiene, 1,7-octadiene, 1,6-octadiene, 1,5-octadiene, 1,4-octadiene and other chain dienes; 1,3,5-heptatriene, 1,3,5-octatriene, 1,3,6-octatriene, 1,4,6-octatriene, 1,3,5-nonatriene, 1,3,7-nonatriene, 1,3,5-decatriene, 1,4,7-decatriene and other chain trienes; 1,5-cyclooctadiene, 1,3-cyclooctadiene, 1,4-cyclohexadiene, 1,3-cyclohexadiene and other cyclic dienes; and 1,3,5-cycloheptatriene, 1,3,5-cyclooctatriene, 1,3,6-cyclooctatriene, 1,4,6-cyclooctatriene, 1,3,5-cyclononatriene, 1,3,7-cyclononatriene, 1,3,5-cyclodecatriene, 1,4,7-cyclodecatreiene and other cyclic trienes.

Moreover, the two $L^0$ in General Formula (1) may be the same or different.

In General Formula (2), $L^1$ represents a hydrogen atom or a halogen atom, and when there are more than one $L^1$, they may be the same or different. $L^1$ is preferably a hydrogen atom. The definition of $L^2$ is the same as that of $L^0$ in General Formula (1).

In General Formula (2), l is an integer from 1 to 5, and is preferably an integer from 3 to 5 from the standpoint of obtaining a trifluorophosphine-ruthenium compound with a high yield. m is an integer from 0 to 4, and is preferably an integer from 0 to 2 from the standpoint of obtaining a trifluorophosphine-ruthenium compound with a high yield. n is an integer from 0 to 2, and is preferably 0 or 1 from the standpoint of obtaining a trifluorophosphine-ruthenium compound with a high yield. l+m+2n is 5 or 6.

Examples of the compound represented by General Formula (1) include ($\eta^4$-1,3-pentadiene) ($\eta^4$-1,3-pentadiene) ruthenium (0), ($\eta^4$-1,3-pentadiene) ($\eta^4$-2,4-hexadiene) ruthenium (0), ($\eta^4$-1,3-pentadiene) ($\eta^4$-1,7-octadiene) ruthenium (0), ($\eta^4$-1,3-pentadiene) ($\eta^6$-1,3,5-heptatriene) ruthenium (0), ($\eta^4$-1,3-pentadiene) ($\eta^6$-1,4,6-octatriene) ruthenium (0), ($\eta^4$-1,3-pentadiene) ($\eta^4$-1,5-cyclooctadiene) ruthenium (0), ($\eta^4$-1,3-pentadiene) ($\eta^4$-1,3-cyclohexadiene) ruthenium (0), ($\eta^4$-1,3-pentadiene) ($\eta^6$-1,3,5-cycloheptatriene) ruthenium (0), ($\eta^4$-1,3-pentadiene) ($\eta^6$-1,3,7-cyclononatriene) ruthenium (0), ($\eta^4$-1,4-hexadiene) ($\eta^6$-1,3,5-heptatriene) ruthenium (0), ($\eta^4$-1,6-heptadiene) ($\eta^6$-1,3,5-heptatriene) ruthenium (0), ($\eta^4$-1,7-octadiene) ($\eta^6$-1,3,5-heptatriene) ruthenium (0), ($\eta^6$-1,3,5-heptatriene) ($\eta^6$-1,3,5-heptatriene) ruthenium (0), ($\eta^6$-1,3,5-heptatriene) ($\eta^6$-1,4,6- octatriene) ruthenium (0), ($\eta^6$-1,3,5-heptatriene) ($\eta^4$-1,5-cyclooctadiene) ruthenium (0), ($\eta^6$-1,3,5-heptatriene) ($\eta^4$-1,3-cyclohexadiene) ruthenium (0), ($\eta^6$-1,3,5-heptatriene) ($\eta^6$-1,3,5-cycloheptatriene) ruthenium (0), ($\eta^6$-1,3,5-heptatriene) ($\eta^6$-1,3,7-cyclononatriene) ruthenium (0), ($\eta^4$-1,3-pentadiene) ($\eta^4$-1,5-cyclooctadiene) ruthenium (0), ($\eta^4$-2,4-hexadiene) ($\eta^4$-1,5-cyclooctadiene) ruthenium (0), ($\eta^4$-1,7-octadiene) ($\eta^4$-1,5-cyclooctadiene) ruthenium (0), ($\eta^6$-1,3,5-heptatriene) ($\eta^4$-1,5-cyclooctadiene) ruthenium (0), ($\eta^6$-1,4,6-octatriene) ($\eta^4$-1,5-cyclooctadiene) ruthenium (0), ($\eta^4$-1,5-cyclooctadiene) ($\eta^4$-1,5-cyclooctadiene) ruthenium (0), ($\eta^4$-1,3-cyclohexadiene) ($\eta^4$-1,5-cyclooctadiene) ruthenium (0), ($\eta^4$-1,5-cyclooctadiene) ($\eta^6$-1,3,5-cycloheptatriene) ruthenium (0), ($\eta^4$-1,5-cyclooctadiene) ($\eta^6$-1,3,5-cyclooctatriene) ruthenium (0), ($\eta^4$-1,4-hexadiene) ($\eta^6$-1,3,5-cyclononatriene) ruthenium (0), ($\eta^4$-1,6-heptadiene) ($\eta^6$-1,3,5-cyclononatriene) ruthenium (0), ($\eta^4$-1,7-octadiene) ($\eta^6$-1,3,5-cyclononatriene) ruthenium (0), ($\eta^6$-1,3,5-heptatriene) ($\eta^6$-1,3,5-cyclononatriene) ruthenium (0), ($\eta^6$-1,4,6-octatriene) ($\eta^6$-1,3,5-cyclononatriene) ruthenium (0), ($\eta^4$-1,5-cyclooctadiene) ($\eta^6$-1,3,5-cyclononatriene) ruthenium (0), ($\eta^4$-1,3-cyclohexadiene) ($\eta^6$-1,3,5-cyclononatriene) ruthenium (0), ($\eta^6$-1,3,5-cycloheptatriene) ($\eta^6$-1,3,5-cyclononatriene) ruthenium (0), ($\eta^6$-1,3,5-cyclononatriene) ($\eta^6$-1,3,7-cyclononatriene) ruthenium (0) and the like.

Examples of the compound represented by General Formula (2) include pentakis(trifluorophosphine) ruthenium (0), ($\eta^4$-1,4-cyclohexadiene) tris(trifluorophosphine) ruthenium (0), ($\eta^4$-1,6-heptadiene) tris(trifluorophosphine) ruthenium (0), (6-$\eta^1$:1-3-$\eta^3$-heptatriene) tris(trifluorophosphine) ruthenium (0), ($\eta^4$-1,4,6-heptatriene) tris(trifluorophosphine) ruthenium (0), ($\eta^4$-1,7-octadiene) tris(trifluorophosphine) ruthenium (0), ($\eta^4$-1,3,5-octatriene) tris(trifluorophosphine) ruthenium (0), ($\eta^4$-1,5-cyclooctadiene) tris(trifluorophosphine) ruthenium (0), ($\eta^4$-1,3,5-cyclooctatriene) tris(trifluorophosphine) ruthenium (0), (6-$\eta^1$:1-3-$\eta^3$-cyclooctatriene) tris(trifluorophosphine)ruthenium (0), ($\eta^4$-1,5-cyclooctadiene) ($\eta^4$-1,3,5-cyclooctatriene) (trifluorophosphine) ruthenium (0), tetrakis(trifluorophosphine) ruthenium (II) dihydride, (difluoro) tetrakis(trifluorophosphine) ruthenium (II), (dichloro) tetrakis(trifluorophosphine) ruthenium (II), (dibromo) tetrakis(trifluorophosphine) ruthenium (II), (diiodo) tetrakis(trifluorophosphine) ruthenium (II), (fluoro) tetrakis (trifluorophoshine) ruthenium (II) hydride, (chloro) tetrakis (trifluorophosphine) ruthenium (II) hydride, tris(trifluorophosphine) ruthenium (III) trihydride, (trifluoro) tris (trifluorophosphine) ruthenium (III), bis(trifluorophosphine) ruthenium (IV) tetrahydride, (tetrafluoro) bis(trifluorophosphine) ruthenium (IV), (tetrachioro) bis(trifluorophosphine) ruthenium (IV), (trifluoro) tetrakis(trifluorophosphine) ruthenium (IV) hydride, (difluoro) tetrakis(trifluorophosphine) ruthenium (IV) dihydride, (dibromo) tetrakis(trifluorophosphine) ruthenium (IV) dihydride, (fluoro) tetrakis (trifluorophosphine) ruthenium (IV) trihydride, (iodo) tetrakis (trifluorophosphine) ruthenium (IV) trihydride and the like.

Fluorine, chlorine, bromine, iodine and the like can be used as halogens. Of these, fluorine, chlorine and bromine are preferred, and fluorine and chlorine are especially preferred.

The hydrogen or halogen used in the aforementioned step can be used for example in gaseous form (for example, hydrogen gas or halogen gas).

In the aforementioned step, the reaction temperature differs according to the type of solvent, but is usually 0 to 200° C., preferably 60 to 180° C., and more preferably 100 to 150° C. The reaction time is usually 0.1 to 48 hours, preferably 0.2 to 24 hours, and more preferably 0.5 to 10 hours.

When a gas is used as a raw material in the reaction, the pressure, which means the total pressure when using multiple types of gasses, during the reaction is usually 0.3 to 5 atm, preferably 0.4 to 3 atm, and more preferably 0.5 to 2 atm.

From the standpoint of reactivity and solubility, preferred examples of the solvent for use in the reaction include water, alcohols, ketones, ethers, esters, nitriles, hydrocarbons and halogenated hydrocarbons. Specific examples of alcohols include methanol, ethanol, n-propanol, isopropanol, butanol and the like. Examples of ketones include acetone, methylethyl ketone, diethyl ketone, dibutyl ketone, t-butylmethyl ketone and the like. Examples of ethers include dimethyl ether, diethyl ether, dibutyl ether, tetrahydrofuran, dioxane and the like. Examples of esters include ethyl acetate, butyl acetate and the like. Examples of nitriles include acetonitrile, propionitrile and the like. Examples of hydrocarbons include heptane, tetradecane and the like. Examples of halogenated hydrocarbons include methylene chloride, chloroform, tetrachloroethane, phenyl chloride, phenyl bromide and the like. The solvent used in the reaction may be one of the aforementioned solvents or a combination of two or more.

After the reaction, solvent extraction, vacuum distillation or recrystallization with a solvent can be performed as necessary to obtain a ruthenium compound.

Examples of solvents for use in extraction and recrystallization include alcohols, ketones, ethers, esters, hydrocarbons, nitriles, halogenated hydrocarbons and the like. Examples of alcohols include methanol, ethanol, n-propanol, isopropanol, butanol and the like. Examples of ketones include acetone, methylethyl ketone, diethyl ketone, dibutyl ketone, t-butylmethyl ketone and the like. Examples of ethers include dimethyl ether, diethyl ether, dibutyl ether, tetrahydrofuran, dioxane and the like. Examples of esters include ethyl acetate, butyl acetate and the like. Examples of hydrocarbons include pentane, hexane, cyclohexane, benzene, toluene and the like. Examples of nitriles include acetonitrile, propionitrile and the like. Examples of halogenated hydrocarbons include methylene chloride, chloroform, tetrachloroethane, phenyl chloride, phenyl bromide and the like.

A combination of two or more of these solvents can be used as the solvent in extraction and recrystallization. In this case, it is desirable to use a combination of at least one selected from the hydrocarbons and halogenated hydrocarbons, and at least one selected from the alcohols, ketones, ethers, esters and nitriles.

The method for producing ruthenium compound of the present invention can also include the step of reacting a compound represented by General Formula (3) described below with an unsaturated hydrocarbon compound having 4 to 10 carbon atoms and at least two double bonds to obtain the compound represented by General Formula (1):

$$RuX_j \qquad (3)$$

(in General Formula (3), X is a halogen atom, and j is an integer of 2 or 3).

In General Formula (3), examples of the halogen atom represented by X include fluorine atom, chlorine atom, bromine atom, and the like.

In this step, the unsaturated hydrocarbon compound having 4 to 10 carbon atoms and at least two double bonds that is reacted with the compound represented by General Formula (3) is similar to $L^0$ in General Formula (1).

In this step, the reaction temperature differs according to the type of solvent, but is usually 0 to 200° C., preferably 60 to 180° C., and more preferably 100 to 150° C. The reaction time is usually 0.1 to 48 hours, preferably 0.2 to 24 hours, and more preferably 0.5 to 10 hours.

From the standpoint of reactivity and solubility, preferred examples of the solvent used in the reaction include water, alcohols, ketones, ethers, esters, nitriles, hydrocarbons, halogenated hydrocarbons and the like. Specific examples of alcohols include methanol, ethanol, n-propanol, isopropanol, butanol and the like. Examples of ketones include acetone, methylethyl ketone, diethyl ketone, dibutyl ketone, t-butylmethyl ketone and the like. Examples of ethers include dimethyl ether, diethyl ether, dibutyl ether, tetrahydrofuran, dioxane and the like. Examples of esters include ethyl acetate, butyl acetate and the like. Examples of nitriles include acetonitrile, propionitrile and the like. Examples of hydrocarbons include heptane, tetradecane and the like. Examples of halogenated hydrocarbons include methylene chloride, chloroform, tetrachloroethane, phenyl chloride, phenyl bromide and the like. The solvent used in the reaction may be one of the aforementioned solvents or a combination of two or more.

EXAMPLES

The present invention is explained in detail below by means of Examples. The present invention is not limited by these Examples.

Synthesis Example 1

Synthesis of ($\eta^4$-1,5-cyclooctadiene) ($\eta^6$-1,3,5-cyclooctatriene) ruthenium (0)

308.57 g of zinc, 500 mL of 1,5-cyclooctadiene and 130 mL of methanol were placed in a nitrogen-substituted and three-necked flask, and were then ultrasound-agitated at 65° C. During ultrasound-agitation at 65° C., 32.95 g of ruthenium trichloride trihydrate and 370 mL of methanol were dripped in over the course of 3 hours in a flow of nitrogen. After dripping, ultrasound-agitation was continued for a further 3 hours at 65° C. After completion of the reaction, the solution was cooled to room temperature and was alumina-filtered in a nitrogen atmosphere, and the filtrate was concentrated under reduced pressure. The resulting blackish-red liquid was subjected to alumina column chromatography using hexane as the developing solvent to produce a clear orange-yellow solution. This solution was concentrated under reduced pressure, and the solvent was distilled off. The obtained substance was then recrystallized with hexane, washed with hexane, and dried under reduced pressure to obtain 24.64 g of orange-yellow needle-shaped crystals. The resulting orange-yellow needle-shaped crystals were confirmed to be ($\eta^4$-1,5-cyclooctadiene) ($\eta^6$-1,3,5-cyclooctatriene) ruthenium (0) based on the $^1$H-NMR spectrum as measured at room temperature at a resolution of 500 MHz with "ADVANCE 500 type $^1$H-NMR" manufactured by Bruker Biospin K.K. using deuterated benzene as the solvent. The yield was 62%.

Example 1

Synthesis of (1,5-cyclooctadiene) tris(trifluorophosphine)ruthenium (0)

A reaction vessel containing 5.08 g of ($\eta^4$-1,5-cyclooctadiene) ($\eta^6$-1,3,5-cyclooctatriene)ruthenium (0) was nitrogen-substituted, and was then agitated after addition of 50 mL of heptane. The solution was cooled to −78° C., and was then depressurized until the pressure inside the system reached 0.01 atm or less. After that, trifluorophosphine was introduced until the pressure reached 0.7 atm, and was then heated and agitated for 2 hours at 60° C. After completion of the reaction, the solution was cooled to −78° C. and dried under reduced pressure to remove the trifluorophosphine. The solution was returned to normal pressure and normal temperature conditions, and was then filtered in a nitrogen atmosphere to obtain 3.96 g of a white solid. The resulting white solid was confirmed to be (1,5-cyclooctadiene) tris(trifluorophosphine) ruthenium (0) based on the $^1$H-NMR spectrum as measured at room temperature at a resolution of 500 MHz with "ADVANCE 500 type $^1$H-NMR" manufactured by Bruker Biospin K.K. using deuterated benzene as the solvent. The yield was 52%.

Example 2

Dihydride tetrakis(trifluorophosphine) ruthenium (II)

A reaction vessel containing 10.02 g of ($\eta^4$-1,5-cyclooctadiene) ($\eta^6$-1,3,5-cyclooctatriene) ruthenium (0) was nitrogen-substituted, and was then agitated after addition of 100 mL of tetradecane. The system was depressurized to 0.01 atm or less, and 0.7 atm of trifluorophosphine and 0.3 atm of hydrogen were introduced. The system was then heated and agitated for 6.5 hours at 150° C. When the internal pressure of the reaction vessel fell by 0.2 atm or more, additional trifluorophosphine and hydrogen were added as necessary until the internal pressure reached 1 atm. After completion of the reaction, the solution was cooled to room temperature and dried under reduced pressure to obtain a light yellow solid in a −78° C. trap. This light yellow solid was returned to normal pressure and normal temperature conditions, and after removal of the colorless transparent liquid of the phase-separated upper layer, was vacuum-distilled at room temperature at 10 torr to obtain 11.31 g of a colorless transparent liquid. The resulting colorless transparent liquid was confirmed to be dihydride tetrakis(trifluorophosphine) ruthenium (II) based on the $^1$H-NMR spectrum as measured at room temperature at a resolution of 500 MHz with "ADVANCE 500 type $^1$H-NMR" manufactured by Bruker Biospin K.K. using deuterated benzene as the solvent. The yield was 78%.

Example 3

Synthesis of (1,5-octadiene) tris(trifluorophosphine) ruthenium (0)

A reaction vessel containing 5.21 g of ($\eta^4$-1,5-octadiene) ($\eta^6$-1,4,7-octatriene) ruthenium (0) was nitrogen-substituted, and was then agitated after addition of 50 mL of heptane. The solution was cooled to −78° C., and was then depressurized until the pressure inside the system reached 0.01 atm or less. After that, trifluorophosphine was introduced until the pressure reached 0.7 atm, and was then heated and agitated for 3 hours at 60° C. After completion of the reaction, the solution was cooled to −78° C. and dried under reduced pressure to remove the trifluorophosphine. The solution was returned to normal pressure and normal temperature conditions, and was then filtered in a nitrogen atmosphere to obtain 2.40 g of a white solid. The resulting white solid was confirmed to be (1,5-octadiene) tris(trifluorophosphine) ruthenium (0) based on the $^1$H-NMR spectrum as measured at room temperature at a resolution of 500 MHz with "ADVANCE 500 type ¹H-NMR" manufactured by Bruker Biospin K.K. using deuterated benzene as the solvent. The yield was 31%.

Example 4

Synthesis of dichlorotetrakis (trifluorophosphine) ruthenium (II)

A reaction vessel containing 10.02 g of ($\eta^4$-1,5-cyclooctadiene) ($\eta^6$-1,3,5-cyclooctatriene) ruthenium (0) was nitrogen-substituted, and was then agitated after addition of 100 mL of tetradecane. The system was depressurized to 0.01 atm or less, and 0.7 atm of trifluorophosphine and 0.3 atm of chlorine were introduced. The system was then heated and agitated for 8 hours at 130° C. When the internal pressure of the reaction vessel fell by 0.2 atm or more, additional trifluorophosphine and chlorine were added as necessary until the internal pressure reached 1 atm. After completion of the reaction, the solution was cooled to room temperature, and was dried under reduced pressure to obtain a light yellow solid in a −78° C. trap. This light yellow solid was returned to normal pressure and normal temperature conditions, and the colorless transparent liquid of the phase-separated upper layer was removed to obtain 8.82 g of a light yellow clear liquid. The resulting light yellow clear liquid was confirmed to be dichlorotetrakis (trifluorophosphine) ruthenium (II) based on the ¹H-NMR spectrum as measured at room temperature at a resolution of 500 MHz with "ADVANCE 500 type ¹H-NMR" manufactured by Bruker Biospin K.K. using deuterated benzene as the solvent. The yield was 57%.

Comparative Example 1

Synthesis of dihydride tetrakis(trifluorophosphine) ruthenium (II) (published example)

A reaction vessel containing 5.03 g of ruthenium trichloride and 10.08 g of copper was vacuumized, and 400 atm of trifluorophosphine and 120 atm of hydrogen were introduced. The reaction vessel was then heated for 20 hours at 250° C. After completion of the reaction, the solution was cooled to room temperature, and was then dried under reduced pressure to remove the trifluorophosphine and hydrogen. The resulting liquid was filtered in a nitrogen atmosphere to obtain 6.58 g of dihydride tetrakis(trifluorophosphine) ruthenium (II) as a light yellow clear liquid. The yield was 60%.

What is claimed is:

1. A method for producing ruthenium compound, comprising the step of reacting a compound represented by General Formula (1) described below with trifluorophosphine, or reacting the compound represented by General Formula (1) described below with trifluorophosphine and at least one selected from hydrogen and halogen to obtain a compound represented by General Formula (2) described below:

$$RuL^0_2 \quad (1)$$

(in General Formula (1), $L^0$ represents an unsaturated hydrocarbon compound having 4 to 10 carbon atoms and at least two double bonds, and the two $L^0$ in General Formula (1) may be the same or different);

$$Ru(PF_3)_l(L^1)_m(L^2)_n \quad (2)$$

(in General Formula (2), $L^1$ represents a hydrogen atom or a halogen atom, and when there are more than one $L^1$, these $L^1$ may be the same or different, $L^2$ represents an unsaturated hydrocarbon compound having 4 to 10 carbon atoms and at least two double bonds, and when there are more than one $L^2$, these $L^2$ may be the same or different, l is an integer from 1 to 5, m is an integer from 0 to 4, and n is an integer from 0 to 2, provided that l+m+2n=5 or 6).

2. The method for producing ruthenium compound according to claim 1, further comprising the step of reacting a compound represented by General Formula (3) described below with an unsaturated hydrocarbon compound having 4 to 10 carbon atoms and at least two double bonds to obtain the compound represented by General Formula (1) described above:

$$RuX_j \quad (3)$$

(in General Formula (3), X is a halogen atom, and j is an integer of 2 or 3).

* * * * *